United States Patent [19]

Stackman

[11] 3,962,299

[45] June 8, 1976

[54] ORGANOPOLYSILOXANE POLYESTERS

[75] Inventor: Robert W. Stackman, Morristown, N.J.

[73] Assignee: Celanese Corporation, New York, N.Y.

[22] Filed: Apr. 25, 1974

[21] Appl. No.: 463,929

[52] U.S. Cl. .................. 260/448.8 R; 260/46.5 E; 260/46.5 G
[51] Int. Cl.² .......................................... C07F 7/18
[58] Field of Search ............... 260/448.8 R, 46.5 E, 260/46.5 G

[56] References Cited
UNITED STATES PATENTS

| | | | |
|---|---|---|---|
| 2,916,507 | 12/1959 | Kerschner et al. | 260/448.8 R X |
| 3,478,075 | 11/1969 | Jack et al. | 260/448.8 R X |
| 3,525,709 | 8/1970 | Somerville et al. | 260/46.5 G |

*Primary Examiner*—Paul F. Shaver

[57] ABSTRACT

Novel organopolysiloxane polyesters are provided by the interaction of bis(2-hydroxyethyl) terephthalate and organohalosilanes.

12 Claims, No Drawings

ORGANOPOLYSILOXANE POLYESTERS

BACKGROUND OF THE INVENTION

The production of bis(hydroxyalkyl) esters of benzenedicarboxylic acids such as bis(2-hydroxyethyl) terephthalate has become of significant commercial importance in recent years because these diesters can be polymerized to form linear super polyesters. These polyesters such as polyethylene terephthalate are widely used in textiles, tire cord, and the like.

The present invention has developed from the investigation of new polymeric compositions derived from bis(2-hydroxyethyl) terephthalate which is now an inexpensive and readily available commercial product. It was deemed desirable to endeavor to introduce the excellent properties of bis(2-hydroxyethyl) terephthalate into polymeric compositions which would have unique properties and versatility in applications commonly served by low molecular weight and high molecular weight polyester compositions.

Thus, it is an object of this present invention to provide novel polymers and resins based on bis(2-hydroxyethyl) terephthalate.

It is another object of the present invention to provide a process for producing polyester polymers which contain repeating siloxane radicals in the polymer structure.

It is still another object of the present invention to provide organopolysiloxane polyesters which range from oils and greases to thermoplastic and thermoset resins.

Other objects and advantages of the present invention will become apparent from the following description and examples.

DESCRIPTION OF THE INVENTION

One or more objects of the present invention are accomplished by a polymerization process which comprises condensing bis(2-hydroxyethyl) terephthalate with an organohalosilane having the formula:

wherein X is a halogen atom (e.g., chlorine, bromine and fluorine); and R is an organic radical containing between 1 and about 22 carbon atoms. By control of the reaction conditions and selection of reactants and additives, the polysiloxane polyesters produced by the process can vary from oils to thermoset resins. These polymeric materials can be produced economically, and find use in a wide range of applications such as lubricants, sealing and caulking compositions, molding compositions, coating resins, elastomers, and the like.

A preferred class of organopolysiloxane polyesters provided by the present invention is characterized by the structural formula:

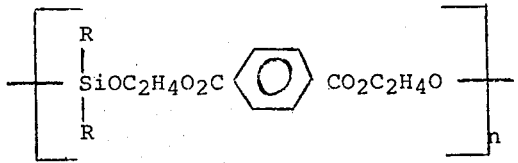

wherein R is selected from hydrocarbon radicals, halo-substituted hydrocarbons and cyano-substituted hydrocarbons, and R contains between 1 and about 10 carbon atoms; $n$ is an integer between 2 and about 10,000, and preferably between about 5 and 1000.

For the purpose of obtaining crosslinked thermoplastic and thermoset polysiloxane polyester resins R can also be halogen. Depending on the physical properties of the polysiloxane polyester resin desired, a crosslinking quantity of trihalosilane or silicon tetrahalide can be incorporated into the polymerization reaction mixture. The crosslinking quantity can vary between about 0.01 up to about 20 weight percent and higher based on the weight of reactants. The inclusion of a polyhydroxy compounds having at least three active hydroxyl groups, such as glycerol or pentaerythritol, is also advantageous as a crosslinking constituent.

With reference to the structural formula hereinabove, R includes such radicals as alkyl radicals, e.g., methyl, ethyl, propyl butyl, octyl and decyl radicals; alkenyl radicals, e.g., vinyl, allyl and hexenyl radicals; cycloaliphatic hydrocarbon radicals, e.g., cyclohexyl cycloheptyl, and cyclohexenyl radicals; aryl radicals, e.g., phenyl, tolyl, xylyl and naphthyl radicals; aralkyl radicals, e.g., benzyl and phenylethyl; halogenated hydrocarbon radicals, e.g., chlorophenyl, tetrachlorophenyl, pentafluorobutyl, trifluoromethylvinyl, and trifluoromethylphenyl radicals; cyanohydrocarbon radicals, e.g., tetra-cyanoethyl, beta-cyanopropyl, delta-cyanobutyl, para-cyanophenyl and ortho-cyanophenyl; and the like.

Illustrative of useful organodihalosilane reactants are dimethyldichlorosilane, dibutyldibromosilane, dibutyldifluorosilane, diisobutyldichlorosilane, methylheptyldichlorosilane, methylallyldichlorosilane, methylphenyldichlorosilane, diphenyldichlorosilane, divinyldichlorosilane, metyl(cyanophenyl)dichlorosilane, and the like. Illustrative of useful organotrihalosilane crosslinking agents are methyltrichlorosilane, tolyltribromosilane, vinyltrichlorosilane, allyltribromosilane, cyanophenyltrichlorosilane, and the like.

Organohalosilanes can be produced by several methods of synthesis. Organohalosilanes are synthesized in one method by high temperature reaction of alkyl or aryl halides with metallic silicon, or with a mixture containing silicon and a metallic catalyst such as copper, silver, zinc, and the like. Mixed alkylacyldihalosilanes can be produced by the organomagnesium synthesis method:

The synthesis methods for producing various alkyl-, alkenyl-, and arylhalosilanes are described in detail in "synthesis of organosilicon monomers" by A. D. Petrov et al. (Consultants Bureau, New York, 1964). A register of organosilane compounds is published by Academic Press (1965) in two volumes entitled "Organosilicon Compounds" by V. Bazant et al.

There are a variety of known methods for producing the bis(2-hydroxyethyl) terephthalate reactant of the invention process. Probably best known and most widely used methods for producing these esters of benzenedicarboxylic acids are those in which the acid is suspended in an inert liquid medium and then reacted with an alkylene oxide in the presence of a catalyst. For example, see U.S. Pat. No. 3,037,049, May 29, 1962 to Alexander A. Vaitekunas which discloses the use of such liquid reaction mediums as aromatic hydrocarbons, ketones and ethers and which also discloses the use of tertiary amine catalysts. Also such patents as Belgian Patent 666,527, Belgian Patent 660,257, British Patent 999,242, British Patent 1,029,669, German Patent 1,157,623, French Patents 1,415,134, 1,430,842, 1,408,874 and Netherlands Patents 6,413,334, 6,506,220 and 6,508,415 disclose esterification processes wherein various reaction media such as hydrocarbons, halohydrocarbons, water, alcohols, nitriles and dimethylformamide-water are disclosed and wherein such catalysts as phosphines, arsines, quaternary ammonium compounds, stibines, amino acids, alkali sulfites, alkali chlorides and alkali nitrates are used as catalysts. More recent advances in methods for producing bis(2-hydroxyl) terephthalate are described in U.S. Pat. Nos. 3,584,031; 3,644,484; and 3,595,471.

In the polymerization process of the present invention, bis(2-hydroxyethyl) terephthalate and the organohalosilane reactant are mixed together under reactive conditions normally in approximately molar equivalent weight quantities. A molar excess of either reactant (e.g., a molar equivalent ratio of 1 to about 5) can be employed if it improves yields or accelerates the composition of the polymerization reaction or has some other desired advantage.

A solvent is employed as a reaction medium. The solvent should be essentially free of moisture, immiscible with water, and non-reactive toward any of the ingredients. Some of the suitable organic solvents are heptane, cyclohexane, benzene, toluene, xylene, naphtha, mineral spirits, perchloroethylene, chlorobenzene, diethyl ether, and butyl acetate. The above list is considered as representative of the suitable organic solvents operable in this invention. The choice of solvent will be determined by other preparation criterion, such as reflux temperature, solubility of reactants and the like.

The bis(2-hydroxyethyl) terephthalate and organohalosilane reactants are mixed together in the presence of an acid acceptor. The reaction is stirred until the reaction has been completed. The length of time the mixture is stirred is not critical and can vary over a wide range, from as short as 1 to 10 minutes to 5 to 10 hours. Although the reaction is usually complete within 30 minutes, longer periods of time such as 1 or 2 hours often are used. Heat is usually not applied to promote reaction and is not a critical factor.

The term acid acceptor applies to a broad range of compounds which will form a complex with acids such as HCl in a non-aqueous system. Most of these acid acceptors are nitrogen-containing organic compounds, but others such as phosphorus and boron organic compounds can be used. Examples of some of the most applicable acid acceptors are pyridine, picolines, morpholine, tributylamine, tertiary amines in general, and dry ammonia. An amount of acid acceptor just necessary to combine with the liberated halogen halide is sufficient. It generally is preferred to use a slight excess of the acid acceptor to insure that there is a sufficient amount of the acceptor in the charge to combine with all the hydrogen halide produced in the polymerization reaction.

The polymerization reaction mixtures which contain a crosslinking constituent such as silicon tetrachloride will produce a polymeric product which precipitates from the reaction medium during the course of the polymerization. In the cases where the organohalosilane reactant contains an olefinic function (e.g., divinyldichlorosilane), the polymerization between bis(2-hydroxyethyl) terephthalate and organohalosilane is carried to completion without inducing crosslinking. The polysiloxane polyester so produced is susceptible to vinyl polymerization conditions via the olefinic function in the organohalosilane moiety in the polymer.

The vinyl polymerization reaction (i.e., the crosslinking reaction) is preferably performed in the presence of a vinyl polymerization catalyst at an elevated temperature to accelerate the process. A catalyst can be incorporated in the reaction mixture in an amount of from about 0.1 to 5 weight percent based on the weight of polymer. Typical vinyl polymerization catalysts include hydrogen peroxide, dicumylperoxide, ditertiary-butylperoxide, benzoylperoxide, and other suitable free radical-generating compounds, and metal derivatives such as cobalt naphthenate.

The following examples are further illustrative of the present invention. The reactants and other specific ingredients are presented as being typical, and various modifications can be devised in view of the foregoing disclosure within the scope of the invention.

EXAMPLE 1

Preparation Of Bis(2-hydroxyethyl) Terephthalate

A 2-liter stirred autoclave was charged with 600 grams of crude terephthalic acid (3.61 moles), 1600 ml. of 2-propyldioxolane reaction medium, 0.11 mole of tetraethyl ammonium terephthalate catalyst and then purged with nitrogen. Liquid ethylene oxide (473 grams, 10.75 mole) was then pumped in and the reactor heated quickly to 155°C. by passing steam through internal coils. After about 3½ minutes the reaction was terminated by pressuring the contents of the autoclave into a vessel where the ethylene oxide was flashed and then the unreacted terephthalic acid removed by filtration. Cooling of the filtrate to about 18°C. gave about 742 grams of crude bis(2-hydroxyethyl) terephthalate.

EXAMPLE 2

Preparation Of Catalyst For Bis(2-hydroxyethyl) Terephthalate Synthesis

A catalyst is prepared from Montrek 600E by mixing 24 grams of the material with 19.5 grams of terephthalic acid as well as 30 ml. of water so that good mixing can be obtained. After stirring the mixture for about 1 hour it is placed on a rotary film evaporator for the removal of the water and a thick solid recovered which is the terephthalic acid salt of the hydroxyethylated polyethyleneimine. Montrek 600E is Dow Chemical Company's designation for a 40% aqueous solution of hydroxyethylated polyethyleneimine which is prepared by reacting polyethyleneimine having a molecular weight of about 40,000 to 60,000 with ethylene oxide.

EXAMPLE 3

Preparation Of Bis(2-hydroxyethyl) Terephthalate

A 3-liter stirred autoclave is charged with 600 grams (3.6 moles) of fiber grade terephthalic acid, 1600 ml. chlorobenzene, 12.4 grams of the terephthalic salt of hydroxethylated polyethyleneimine as prepared in Example 2, and then purged with nitrogen. Liquid ethylene oxide (8.6 moles) is then pumped in and the reactor heated to 175°C. by passing steam through internal coils. The temperature is maintained at 175°C. for about 30 minutes with the pressure varying during the period from about 215 p.s.i.g. at the beginning of the period to 80 p.s.i.g. at the end of the period. After the thirty minute period the reaction is terminated by pressuring the contents of the autoclave into a vessel where ethylene oxide is flashed and then the unreacted terephthalic acid and other solids removed by filtration. Cooling of the filtrate to about 30°C. yields about 760 grams of bis(2-hydroxyethyl) terephthalate (dry basis). Conversion of terephthalic acid charged to the diester product is about 91 mole percent.

EXAMPLE 4

Preparation Of A Polysiloxane Polyester

To a 500 ml. flask is added 25.4 grams (0.1 mole) of bis(2-hydroxyethyl) terephthalate, 100 grams of pyridine and 100 ml. of benzene. A solution of 25.3 grams of diphenyldichlorosilane in 50 ml. of benzene is added dropwise to the reaction mixture. At the end of the addition the mixture is stirred for an additional hour, then filtered and the solvent removed under vacuum to yield 43 grams of a pale yellow viscous oil.

EXAMPLE 5

Preparation Of A Polysiloxane Polyester

To 500 ml. flask is added 25.4 grams (0.1 mole) of bis(2-hydroxyethyl) terephthalate, 100 grams of pyridine and 100 ml. of benzene. To this reaction mixture is added 12.9 grams (0.1 mole) of dichlorodimethylsilane in 50 ml. of benzene. The mixture is stirred for one hour after the addition is completed, then it is filtered and the solvent is removed under vacuum to yield 30 grams of a colorless viscous oil.

EXAMPLE 6

Crosslinked Polysiloxane Polyester

To a 250 ml. flask is added 23 grams (0.09 mole) of bis(2-hydroxyl) terephthalate, 0.9 gram (0.01 mole) of glycerine, 100 ml. of benzene and 16 grams of pyridine. To the reaction mixture dichlorodiphenylsilane (0.15 mole) is added dropwise. The mixture is stirred for three hours at reflux, then filtered and the solvent removed to yield 49 grams of heavy grease.

The procedure is repeated employing 20.3 grams (0.08 mole) bis(2-hydroxyethyl) terephthalate and 1.8 grams (0.02 mole) of glycerine. A yield of 42.5 grams is recovered. The product is a clear flexible polymer which is moldable at room temperature.

The procedure is repeated employing 17.8 grams (0.07 mole) of bis(2-hydroxyl) terephthalate and 2.7 grams (0.03 mole) of glycerine. The product is a glass-like solid at room temperature. Heating the product to about 60°C. converts it into an elastomeric material.

EXAMPLE 7

Crosslinked Polysiloxane Polyester

In a manner similar to Example 4, 25 grams of bis(2-hydroxyethyl) terephthalate, 100 grams of pyridine and 100 ml. of benzene are added to a flask. A solution of 25 grams of divinyldichlorosilane in 50 ml. of benzene is added dropwise to the reaction mixture. After completion of the reaction period, the reaction mixture is filtered and treated with one gram of cobalt naphthenate solution (6% cobalt). The mixture is spread on a plate and heated to 60°C. in an air oven overnight. The coating converts into a tough flexible film.

What is claimed is:

1. A polymerization process for producing an organopolysiloxane polyester which comprises condensing bis(2-hydroxyethyl) terephthalate with an organohalosilane having the formula:

$$X-\underset{\underset{R}{|}}{\overset{\overset{R}{|}}{Si}}-X$$

wherein X is a halogen atom; and R is selected from halogen and hydrocarbon radicals, halo-substituted hydrocarbons and cyano-substituted hydrocarbons containing between 1 and about 22 carbon atoms.

2. A process according to claim 1 wherein the reactants are present in about molar equivalent weights.

3. A polymerization process for producing an organopolysiloxane polyester which comprises condensing bis(2-hydroxyethyl) terephthalate with dimethyldichlorosilane.

4. A polymerization process for producing an organopolysiloxane polyester which comprises condensing bis(2-hydroxyethyl) terephthalate with diphenyldichlorosilane.

5. A polymerization process for producing an organopolysiloxane polyester which comprises condensing bis(2-hydroxyethyl) terephthalate with divinyldichlorosilane.

6. A process according to claim 1 wherein there is included as a reactant a crosslinking quantity of a member selected from organotrihalosilane, silicon tetrahalide, and poylols having at least three reactive hydroxyl groups.

7. A process according to claim 5 wherein as an additional step, the organopolysiloxane polyester is crosslinked in the presence of a vinyl polymerization catalyst.

8. A organopolysiloxane polyester characterized by the structural formula:

$$\left[ \underset{\underset{R}{|}}{\overset{\overset{R}{|}}{Si}} OC_2H_4O_2C \underset{}{\bigcirc} CO_2C_2H_4O \right]_n$$

wherein R is selected from hydrocarbon radicals, halo-substituted hydrocarbons and cyano-substituted hydrocarbons, and R contains between 1 and about 10 carbon atoms; $n$ is an integer between 5 and about 1000.

9. An organopolysiloxane polyester in accordance with claim 8 wherein R is a methyl radical.

10. An organopolysiloxane polyester in accordance with claim 8 wherein R is a phenyl radical.

11. An organopolysiloxane polyester characterized by the structural formula:

$$\left[ \underset{\underset{R}{|}}{\overset{\overset{R}{|}}{Si}} OC_2H_4O_2C \underset{}{\bigcirc} CO_2C_2H_4O \right]_n$$

wherein R is selected from halogen and hydrocarbon radicals, halo-substituted hydrocarbons and cyano-substituted hydrocarbons containing between 1 and about 10 carbon atoms; and $n$ is an integer between 5 and about 1000.

12. An organopolysiloxane polyester in accordance with claim 8 wherein R is a vinyl radical.

* * * * *